US00PP10529P

United States Patent [19]

Pouw

[11] Patent Number: Plant 10,529

[45] Date of Patent: Aug. 4, 1998

[54] HYBRID TEA ROSE PLANT NAMED 'RUIWITUN'

[75] Inventor: A. A. Pouw, De Kwakel, Netherlands

[73] Assignee: De Ruiter's Nieuwe Rozen B.V., De Kwakel, Netherlands

[21] Appl. No.: 759,608

[22] Filed: Dec. 5, 1996

[51] Int. Cl.[6] ..... A01H 5/00

[52] U.S. Cl. ..... Plt./15

[58] Field of Search ..... Plt./15, 14

*Primary Examiner*—Howard J. Locker

*Attorney, Agent, or Firm*—Christie, Parker & Hale, LLP

[57] ABSTRACT

A new variety of hybrid tea rose plant producing white to yellow-white colored flowers of good form and suitable for growing under glass.

1 Drawing Sheet

BACKGROUND OF THE INVENTION

The present invention relates to a new and distant variety of rose plant of the hybrid tea rose class which was created by crossing undistributed, unnamed and unpatented seedlings as seed and pollen parents in De Kwakel, Holland. The varietal denomination of the new variety is 'Ruiwitun'. The new variety was isolated and asexually reproduced by budding in Holland.

SUMMARY OF THE INVENTION

Among the novel characteristics possessed by this new variety which distinguish it from its parents and all other varieties of which I am aware are its attractive white to yellow-white flowers of good form borne on a floriferous plant with long stems and suitable for production of cut flowers under glass. The new variety has been reproduced through propagation by cuttings, grafting, budding and micropropagation.

Asexual reproduction by budding, cuttings, grafting and micropropagation of the new variety as performed in Holland shows that the foregoing and other distinguishing characteristics come true to form and are established and transmitted through succeeding propagations.

BRIEF DESCRIPTION OF ILLUSTRATION

The accompanying illustration shows typical specimens of the vegetative growth and flowers of the new variety in different stages of development depicted in color as nearly true as it is reasonably possible to make the same in a color illustration of this character.

DESCRIPTION OF THE NEW VARIETY

The following is a detailed description of the new variety, with color terminology in accordance with The Royal Horticultural Society Colour Chart (R.H.S.C.C.) and horticultural terminology in accordance with standard terminology used in UPOV-approved horticultural guideline. The terminology used in color descriptions herein refers to plate numbers in the aforementioned color chart. Phenotypic expression may vary depending upon growing conditions under different climate, soil, and cultivation conditions.

Parentage: Seed and pollen parents are seedlings.
Class: Hybrid Tea.

As can be seen in the accompanying detail illustration there is shown a new shoot and bud, 1; compound three, five and seven leaflet leaves, 2, 3 and 4, respectively; a stem, 5; buds, 6 and 7; a flower, 8, about one-third open; and a flower, 9, more fully open. Also shown are flower stems 10, 11 and 12, with reproductive organs displayed.

The following further horticultural description is based on observations made of specimens grown under glass in Holland.

Flower

Blooming habit: Nearly continuous.

A. Bud:

(1) *Size.*—Medium, about 4 to 4½ cm long and about 3 to 3½ cm wide, after sepals fall (2) *Form.*—Ovate (shape of longitudinal section just before separation of sepals); urn-shaped after sepals part (3) *Color.*—As sepals divide, near 11D to 11C (4) *Sepals.*—Longer than bud, foliated sepals: Underside near 143C. Top near 184C.

(5) *Peduncle.*—Long: erect, strong, color near 148B.

B. Bloom:

*Flower.*—Medium; viewed from above — star shaped; viewed from side — (a) upper part of fully opened flower, flattened convex; (b) lower part of fully opened flower, flat.

(1) *Size.*—Average size when fully expanded — about 10 to 11 cm.

(2) *Borne.*—Singly, one to a stem.

(3) *Form.*—Pointed center, exhibition type, somewhat flat top, spiral imbricated, most petals reflex to points, some curl under (4) *Petalage.*—About 23; number of petaloids about 10, from outside to inward becoming smaller; size of petaloids about 4.5×3.5 cm to about 2×1 cm; petaloids are irregularly folded.

(5) *Color.*—After sepals part and petals unfurl color of petal top surface appears near 11D to near 155A, to 155B darker where petals bunch near 11B; petal undersurface near 11D; zone of petal attachment near 2C. Overall tonality from a distance is attractive white to yellow-white.

(6) *Peduncle.*—Generally smooth.

(7) *Fragrance.*—Weak.

(8) *Length of stem**.—About 70 cm from last cut.

(9) *Production**.—About 175 blooms per $m^2$ per year.

*Average only, depends on circumstances of cultivation.

Petals:

(1) *Texture.*—Crisp.

(2) *Appearance.*—Inside velvety and outside satiny.

(3) *Form and size.*—Broad, medium, weak undulation of margin.

(4) *Arrangement.*—Regularly arranged, imbricated.
(5) *Petaloids.*—Several, about 10.
(6) *Lasting quality.*—Vaselife varies from about 18 to 20 days; bloom on plant lasts for about 16 days and then the petals drop; flower opens quite rapidly.

Reproductive Organs

A. Stamens, filaments and anthers:
Arrangement and color: Regularly arranged around styles; color of filaments—yellow.
B. Pollen:
*Color.*—Near 11B.
C. Styles: Long, stigma above mouth of receptacle, light yellow.
D. Stigmas: White to light yellow, positioned below anthers.
E. Hip: Funnel-shaped; medium seed vessel at petal fall; color green to orange; up to about 2 cm.

Plant

A. Form: Narrow, bushy, average disease resistance.
B. Growth: Vigorous; about 1.5 m in height, about 0.5 in width.
C. Foliage: Compound 3, 5 and 7 leaflets.
(1) *Size.*—Terminal leaflet about 8 to 9 cm.
(2) *Quantity.*—Abundant.
(3) *Color.*—Juvenile foliage — upper side near 183A; underside near 183B; weak to medium anthocyanin coloration. (shoot about 20 cm long); mature leaf color — upper side near 139A underside near 139B to 139C.
(4) *Shape.*—Elliptic.
(5) *Texture.*—Upper side is semi-glossy; underside is matte.
(6) *Edge.*—Serrate to serrulate.
(7) *Serration.*—Ordinary, acute to cuspidate apices.
(8) *Leaf stem.*—Color — medium green, near 139B to 147A.
(9) *Stipules.*—Short, simple, medium green, with dark tinge on sides and top; distinct auricle.
(10) *Leaflets.*—Cross section — slight concave: weak undulation of margin; terminal leaflet — long length and medium width; rounded base.
D. Wood:
(1) *New wood.*—Color — young shoots have weak to medium anthocyanin.
(2) *Old wood.*—Color — medium green, near 147A to 147B.
E. Prickles (thorns):
(1) *Prickles.*—Top about 40 cm of stem has no prickles, lower part of stem (about 30 cm) has prickles; Shape of lower side — concave; Length — short prickles absent or very few, long prickles few; Position — irregular.
F. Disease resistance: Somewhat susceptible to mildew.

What is claimed is:

1. A new and distinct plant of the hybrid tea rose class, substantially as shown and described.

* * * * *

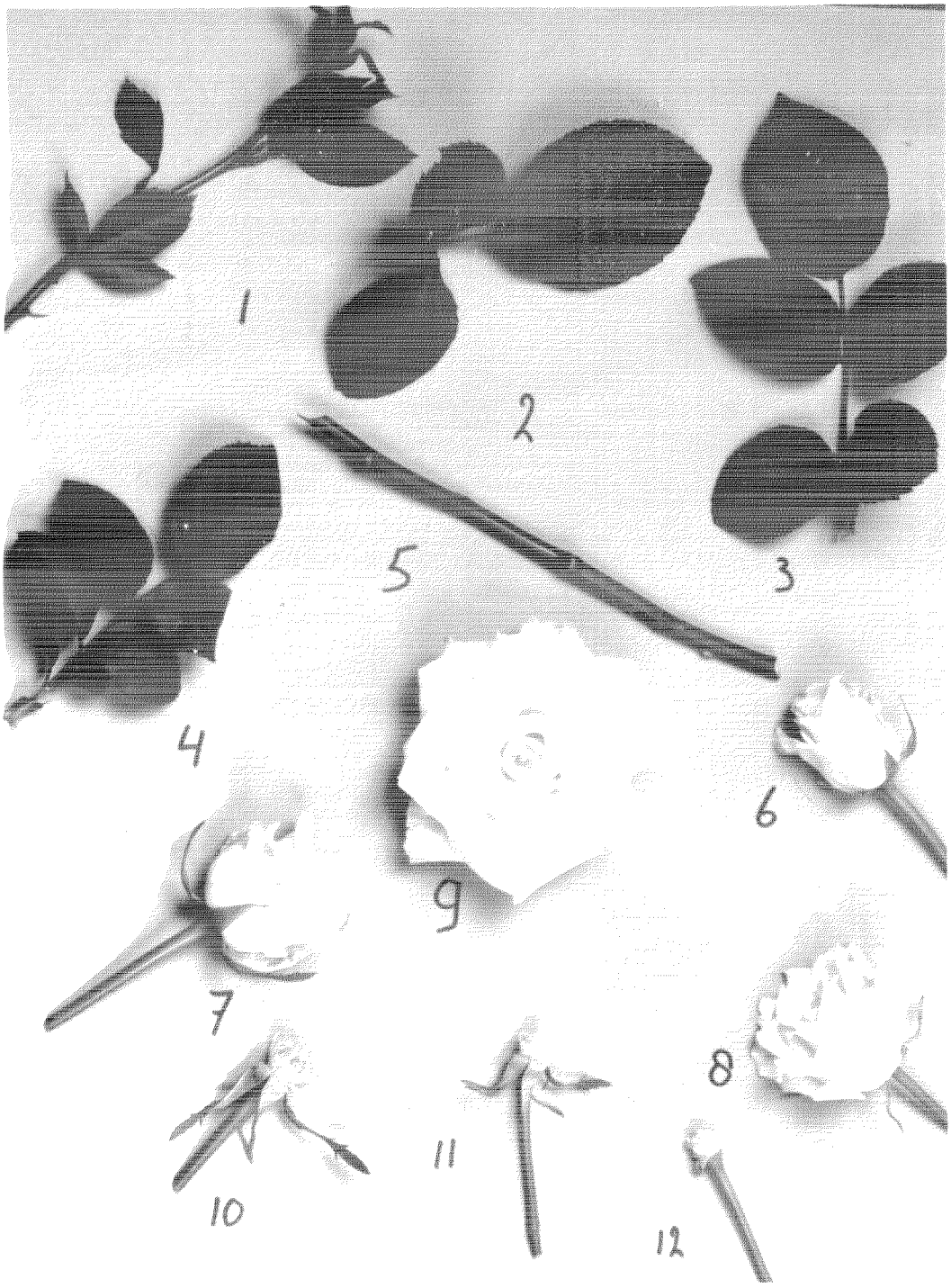
1
2
3
4
5
6
7
8
9
10
11
12

UNITED STATES PATENT AND TRADEMARK OFFICE

CERTIFICATE OF CORRECTION

PATENT NO. : Plant 10,529
DATED : August 4, 1998
INVENTOR(S) : A. A. Pouw

It is certified that error appears in the above-identified patent and that said Letters Patent is hereby corrected as shown below:

Column 3, line 28, after "coloration" delete the period.

Signed and Sealed this

Twenty-ninth Day of February, 2000

*Attest:*

Q. TODD DICKINSON

*Attesting Officer*

*Commissioner of Patents and Trademarks*